US006770883B2

(12) United States Patent
Mc Neal et al.

(10) Patent No.: US 6,770,883 B2
(45) Date of Patent: Aug. 3, 2004

(54) SAMPLE LEVEL DETECTION SYSTEM

(75) Inventors: Jack D. Mc Neal, Long Beach, CA (US); Yagang Liu, Irvine, CA (US); Mary S. Adzich, Yorba Linda, CA (US)

(73) Assignee: Beckman Coulter, Inc., Fullerton, CA (US)

( * ) Notice: Subject to any disclaimer, the term of this patent is extended or adjusted under 35 U.S.C. 154(b) by 0 days.

(21) Appl. No.: 10/060,751

(22) Filed: Jan. 30, 2002

(65) Prior Publication Data

US 2003/0141456 A1 Jul. 31, 2003

(51) Int. Cl.[7] .................................................. G01J 5/02
(52) U.S. Cl. ..................................... 250/341.1; 356/39
(58) Field of Search .............................. 250/577, 357.1, 250/341.1; 356/39, 40, 436; 73/290 R

(56) References Cited

U.S. PATENT DOCUMENTS

| 3,898,433 | A | | 8/1975 | Sallet |
| 4,100,416 | A | * | 7/1978 | Hirschfeld ............... 250/461 B |
| 4,303,336 | A | * | 12/1981 | Cullis ........................... 356/39 |
| 4,350,441 | A | * | 9/1982 | Wicnienski ................... 356/40 |
| 4,704,029 | A | | 11/1987 | Van Heuvelen |
| 4,882,492 | A | | 11/1989 | Schlager |
| 5,013,156 | A | | 5/1991 | Murphy |
| 5,115,133 | A | | 5/1992 | Knudson |
| 5,183,042 | A | | 2/1993 | Harjunmaa et al. |
| 5,359,192 | A | | 10/1994 | Williams et al. |
| 5,370,114 | A | | 12/1994 | Wong et al. |
| 5,502,559 | A | | 3/1996 | Powell et al. |
| 5,547,577 | A | * | 8/1996 | Vogler et al. ................ 210/511 |
| 5,601,079 | A | | 2/1997 | Wong et al. |
| 5,737,076 | A | | 4/1998 | Glaus et al. |
| 5,817,007 | A | | 10/1998 | Fodgaard et al. |
| 6,055,050 | A | | 4/2000 | Skiffington |
| 6,070,093 | A | | 5/2000 | Oosta et al. |
| 6,157,442 | A | | 12/2000 | Raskas |
| 6,195,158 | B1 | * | 2/2001 | Cadell et al. ................... 356/39 |
| 6,446,515 | B2 | * | 9/2002 | Cole et al. ............... 73/863.21 |
| 2002/0067476 | A1 | * | 6/2002 | Kawano ....................... 356/39 |

OTHER PUBLICATIONS

International Search Report for International Application PCT/US03/02916.

* cited by examiner

Primary Examiner—Diego Gutierrez
Assistant Examiner—Tania Courson
(74) Attorney, Agent, or Firm—William H. May; D. David Hill; Sheldon & Mak, LLP

(57) ABSTRACT

A method and apparatus for detecting the level of red blood cells, plasma or serum, and organic separation gel in a test tube covered with multiple labels is provided. Visible and infrared light beams are projected onto a test tube. The portions of the light beams that pass through the test tube are detected as a function of position along the vertical axis of the test tube. The levels of the interfaces are then calculated from the detected portions.

25 Claims, 5 Drawing Sheets

SAMPLE LEVEL DETECTION SYSTEM

BACKGROUND

When a test tube containing a blood sample arrives at a laboratory where tests are to be performed on the sample, it must be determined whether there is a large enough sample to conduct the ordered tests. More specifically, after the sample is separated in a centrifuge, it is necessary to determine the amount of red blood cells and serum or plasma, in the sample.

Sometimes, organic separation gel is added into the tube in order to store the sample. The gel provides a hydrophobic barrier between the serum and the red blood cells and thereby prevents the red blood cells from metabolizing the components of the serum. Therefore, it is also necessary to determine if gel is present in the sample.

These tasks are traditionally performed by visual inspection. However, generally, before the test tube arrives at the laboratory, many labels are placed on the test tube. Several layers of labels make visual inspection very time consuming and difficult, if not impossible. Accordingly, there is a need to easily, quickly, inexpensively, reliably, and safely determine if there is a large enough sample present in a test tube that is covered in labels to conduct required tests.

SUMMARY

The present invention meets this need by providing a method for detecting interfaces in a container made up of a material and having a vertical axis and containing an upper layer of serum or plasma and a lower layer of cells. The container can also contain a middle layer of gel and have a cap. The container can be a test tube made up of plastic or glass.

A first detecting light beam, which is substantially transmitted by serum, plasma, labels and the material but substantially blocked by the cells, is projected onto the container. A portion of the first detecting light beam is transmitted through the container. A second detecting light beam, which is substantially blocked by serum, plasma, and cells, but substantially transmitted by the material and labels, is also projected onto the container. A portion of the second detecting light beam is transmitted through the container. Lasers, either directly or through fiber optic cables, can project the light beams.

Then, the portion of the first detecting light beam that is transmitted through the container and no significant portion of the second detecting light beam is detected as a function of position along the vertical axis of the container. Likewise, the portion of the second detecting light beam that is transmitted through the container and no significant portion of the first detecting light beam is detected as a function of position along the vertical axis of the container. Then, the location of interfaces is determined from the detected portions.

The first and second detecting light beams can be projected by respective projectors, and detected by respective detectors. The light beams preferably are substantially perpendicular to the longitudinal axis of the container, and can be coplanar.

The present invention further provides an apparatus for detecting the location of at least one interface in a container made up of a material and having a vertical axis and containing an upper layer of serum or plasma and a lower layer of cells. A first projector projects onto the container a first detecting light beam that is substantially transmitted by serum and plasma and the material but is substantially blocked by the cells. A portion of the first detecting light beam is transmitted through the container. A second projector projects onto the container a second detecting light beam that is substantially blocked by serum, plasma, and cells, but is substantially transmitted by the material. A portion of the second detecting light beam is transmitted through the container.

A first detector detects, as a function of position along the vertical axis of the container, the portion of the first detecting light beam that is transmitted through the container. A second detector detects, as a function of position along the vertical axis of the container, the portion of the second detecting light beam that is transmitted through the container. A processor is operably attached to the detectors and determines the location of interfaces from the detected portions.

DRAWINGS

These and other features, aspects, and advantages of the present invention will become better understood with reference to the following description, appended claims, and accompanying drawings, where:

DESCRIPTION

The invention provides a sample level detection system that uses both visible and infrared light to take advantage of the spectral properties of serum, red blood cells, and gel.

Figure 1:
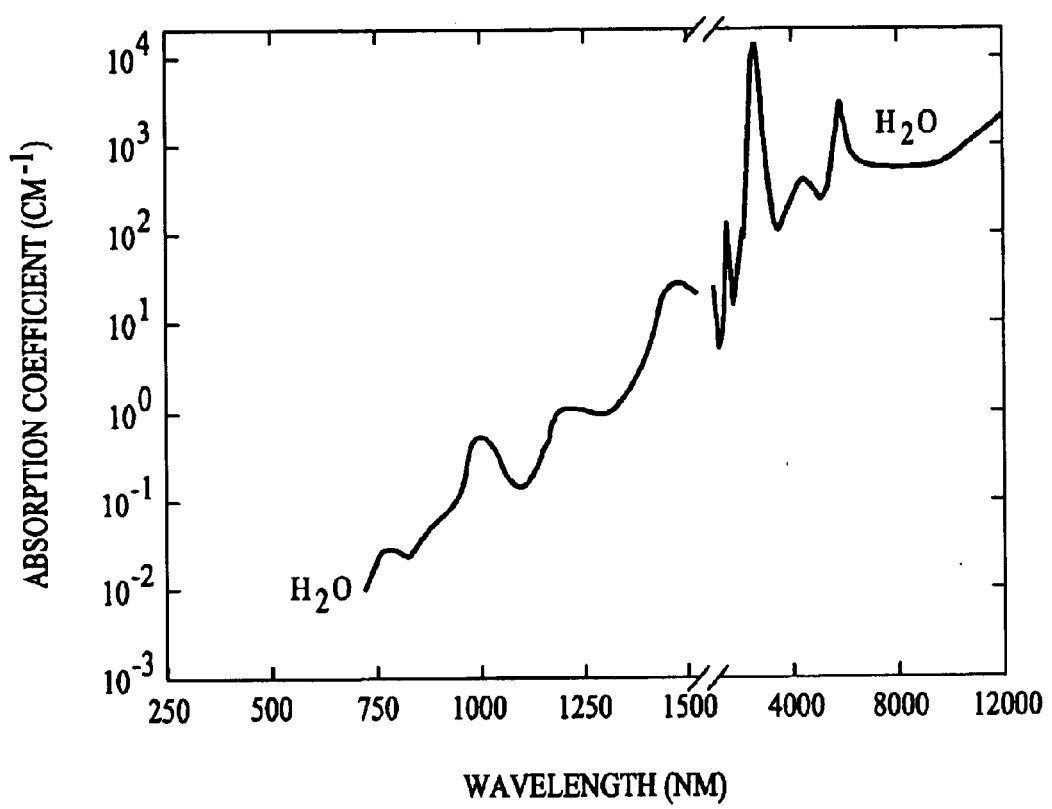
FIG. 1 is a graphical representation of the water absorption spectrum.

Since serum is water based, its absorption characteristic is essentially the same as water. FIG. 1 shows the water absorption spectrum. As can be seen, at a wavelength of 1500 nm, the water absorption coefficient is about 20 cm$^{-1}$. For a 1 cm water thickness, the transmittance is about $2 \times 10^{-9}$, which means that water is a substantially opaque material for light at this wavelength. Therefore, if labels on the tube wall modulate infrared light intensity by less than 5–6 OD, it is still possible to sense the serum presence through the labels.

The invention takes the spectral measurements of the contents of a test tube or other container that is constructed of a material that is transparent to both visible and infrared light while significantly suppressing label interference. Hence, the interfaces of the serum, gel, and red blood cells are detectable even in the presence of multiple labels. The container material is typically, but not necessarily, a soda-lime, borosilicate, or Pyrex® glass or a polypropylene, polymethylpentene, polycarbonate, etc. plastic.

The gel is typically, but not necessarily, a polymer gel with a specific gravity of about 1.04. Further, the gel is typically, but not necessarily, a silicon gel containing one of the polydimethylsiloxane-polyethyleneoxide copolymer gelled with dibenzylidine sorbitol in the presence of water or alcohol as disclosed in U.S. Pat. No. 5,547,577, which is incorporated herein by reference. The gel may be mixed with silica or glass particles that accelerate clotting. Alternatively, the invention can also be used with a plastic filter, as opposed to gel, that separates the cells and the serum.

Figure 2:
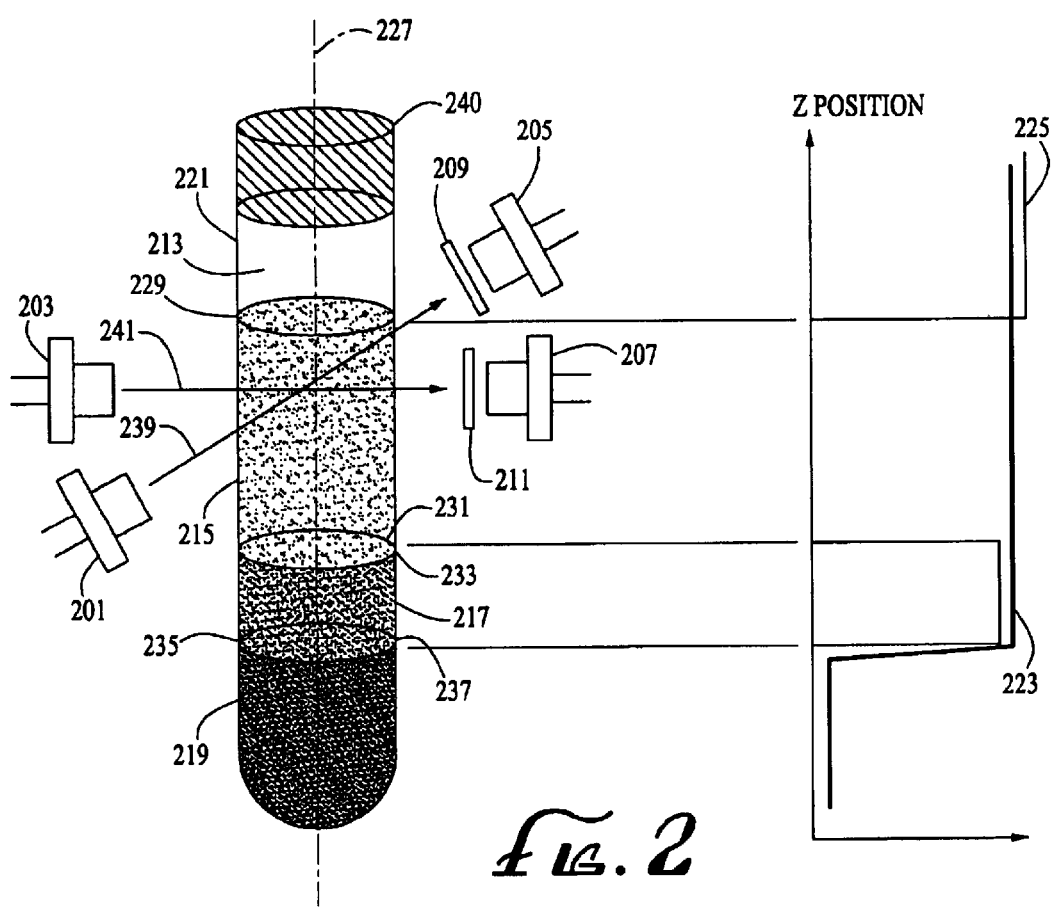
FIG. 2 illustrates a system according to the present invention being used to analyze a sample tube with separation gel present.

Referring now to FIG. 2, serum 215 and gel 217 are mostly transparent to visible light while red blood cells 219 are substantially opaque. Further, gel 217 is transparent to infrared light while red blood cells 219 and serum 215 are substantially opaque. Accordingly, when the sample tube 221 has gel 217 to separate the serum 215 and red blood cells 219, it is possible just using infrared light to "see through" different sections. The infrared light reading 225 is strong when the infrared light beam 241 passes through air 213, drops when the infrared light beam is directed toward the serum 215, is relatively strong when directed toward the gel 217, and drops again when directed toward the read blood cells 219.

Figure 3:
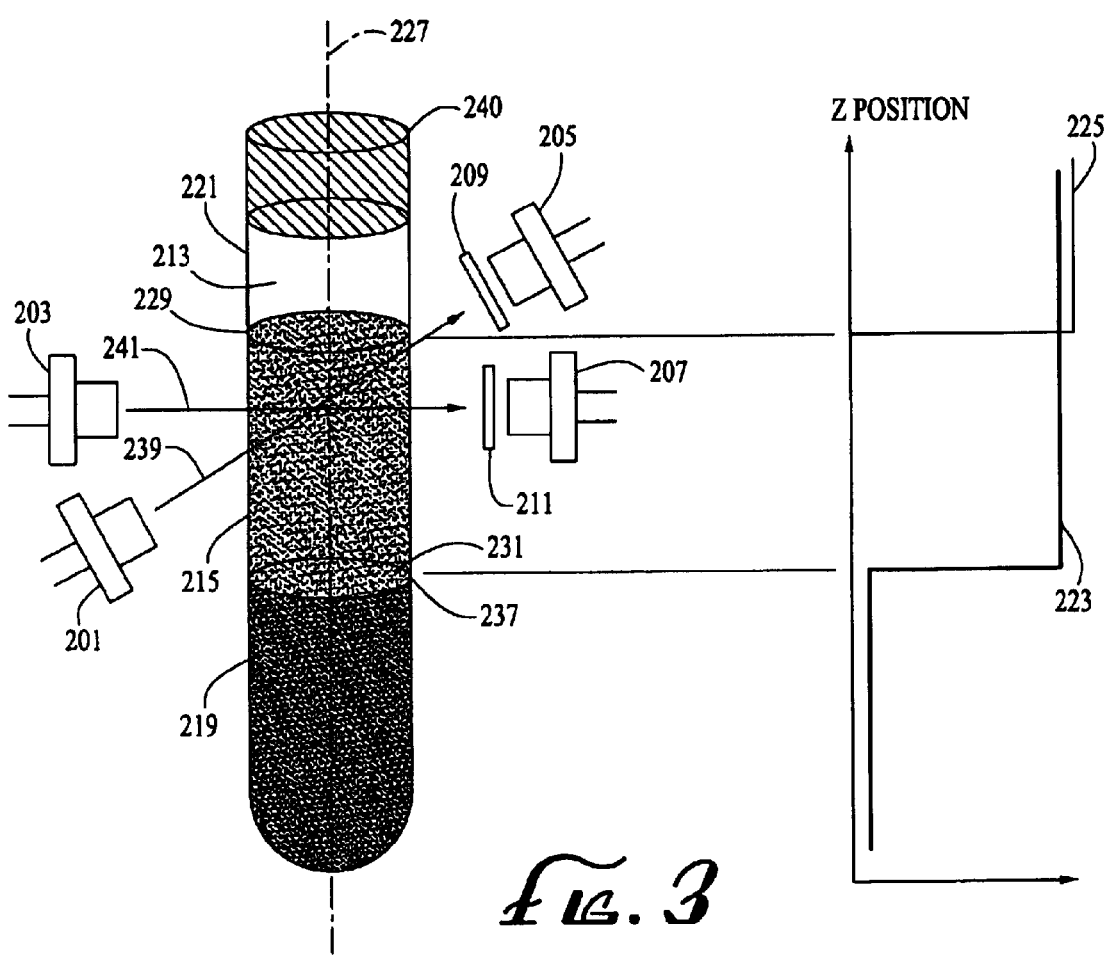
FIG. 3 illustrates the system of FIG. 2 being used with a sample tube not containing gel.

Referring now to FIG. 3, when the sample tube 221 has no gel to separate the serum 215 and red blood cells 219, the infrared light is totally absorbed by both media. Therefore, only the interface between the air 213 and the serum 215 can be sensed by infrared light. However, because serum 215 is mostly transparent to visible light, while red blood cells 219 are basically opaque, a combination of two wavelengths of light can detect every interface in the sample tube. The infrared light reading 225 is strong when the infrared light beam 241 passes through air 213 but drops when the infrared light beam is projected toward the serum 215. The reading remains low while the infrared light beam 241 is projected toward the cells 219. The visible light reading 223 is strong while the visible light beam 239 is projected toward the air 213 and serum 215 but drops when the visible light beam is projected toward the cells 219.

Now, referring to FIGS. 2–5, in a preferred embodiment, but not required, two light sources, a visible light source 201 and an infrared light source 203 scan a test tube 221 from top to bottom. The visible light is preferably, although not necessarily, in the range of about 300 nm to about 1200 nm. If the wavelength is less than 300 nm, it may be absorbed by the container if the container is constructed of plastic. If the wavelength is over 1200 nm, water will start to absorb the light. More preferably, however, the visible light has a wavelength in the range of about 400 to about 1000 nm. The range of about 500 to about 800 nm is most preferable, although not required, as these wavelengths can be obtained with low cost lasers. Specifically, wavelengths of 416 nm, 635 nm, 670 nm, and 780 nm are preferred as lasers of these wavelengths are readily available, although they are not required.

The long wavelength light preferably, but not necessarily falls within the range of about 1.4 $\mu$m to about 6.8 $\mu$m since the gel and some plastic materials have absorption bands in the wavelength range of approximately 2.8 $\mu$m–3.8 $\mu$m, more preferably the long wavelength light is from about 1.45 $\mu$m to about 2.8 $\mu$m, or from about 3.8 $\mu$m to about 6.8 $\mu$m. The bottom limit of the long wavelength light is about 1.4 $\mu$m to be sure that the serum absorbs the light. The maximum limit is set by what wavelength goes through the container.

Laser diodes and LED's are preferred light sources, but are not required. Some of the major advantages of using laser diodes in conjunction with the invention are there is no signal cross talk and the light passes through labels. For example, a GaAlP laser diode ($\lambda$=670 nm) with 30 mW of power may be used as a visible or "short wavelength" light source and a GaAsP laser diode ($\lambda$=1550 nm) with 6 mW of power may be used as an infrared or "long wavelength" light source.

Figure 5:
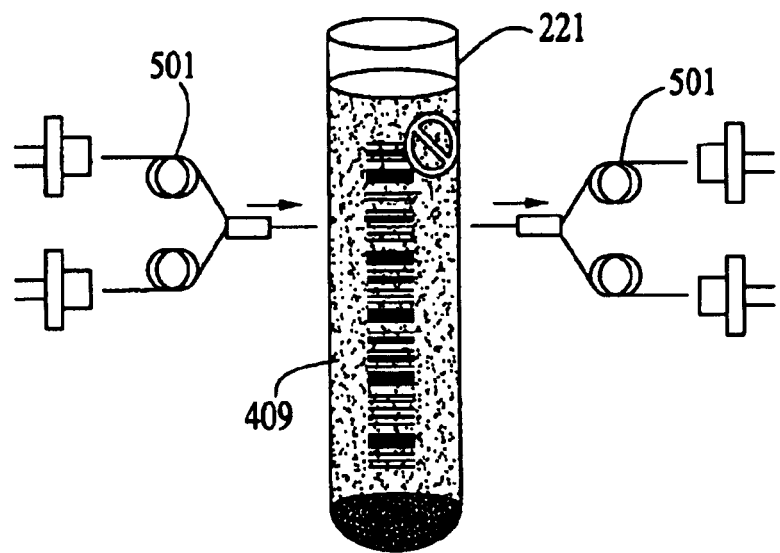
FIG. 5 is a partial front elevation view of an alternative preferred sample level detection system utilizing fiber optic connectors according to the present invention.

In a preferred alternative embodiment, any kind of semiconductor laser of proper wavelength can be used, including Nichia's violet laser diode. Alternatively, any gas or solid state laser of a proper wavelength may be used, such as He—Ne ($\delta$=633 nm), Ar+($\delta$=488 nm or 514 nm or mixed), Nd:YAG ($\delta$=1.06 $\Phi$m or 0.53 $\Phi$m). In a further alternative preferred embodiment, as illustrated in FIG. 5, fiber optic connectors are used to confine the light path. A high intensity light with a filter can also be used. A halogen lamp can be used as a light source; however, serum is mostly transparent to the near infrared region of light (i.e. wavelengths about 800 to about 1200 nm) and the light leaks into the infrared detector even if a 3–5 OD blocking filter is used. Therefore, the 9 OD contrast of 1500 nm light between serum and air would be significantly reduced and may be unable to suppress label interference.

Two detectors, a visible light detector 209 and an infrared light detector 211, are positioned so that they detect the portions of visible and infrared light beams 239 and 241, respectively, that pass through the test tube 221 as a function of position along the vertical axis 227 of the test tube. Preferably, but not necessarily, the detectors that are used are an Si PIN photodiode as the visible or "short wavelength" light detector and an InGaAs photo-detector as an infrared or "long wavelength" light detector.

Figure 4:
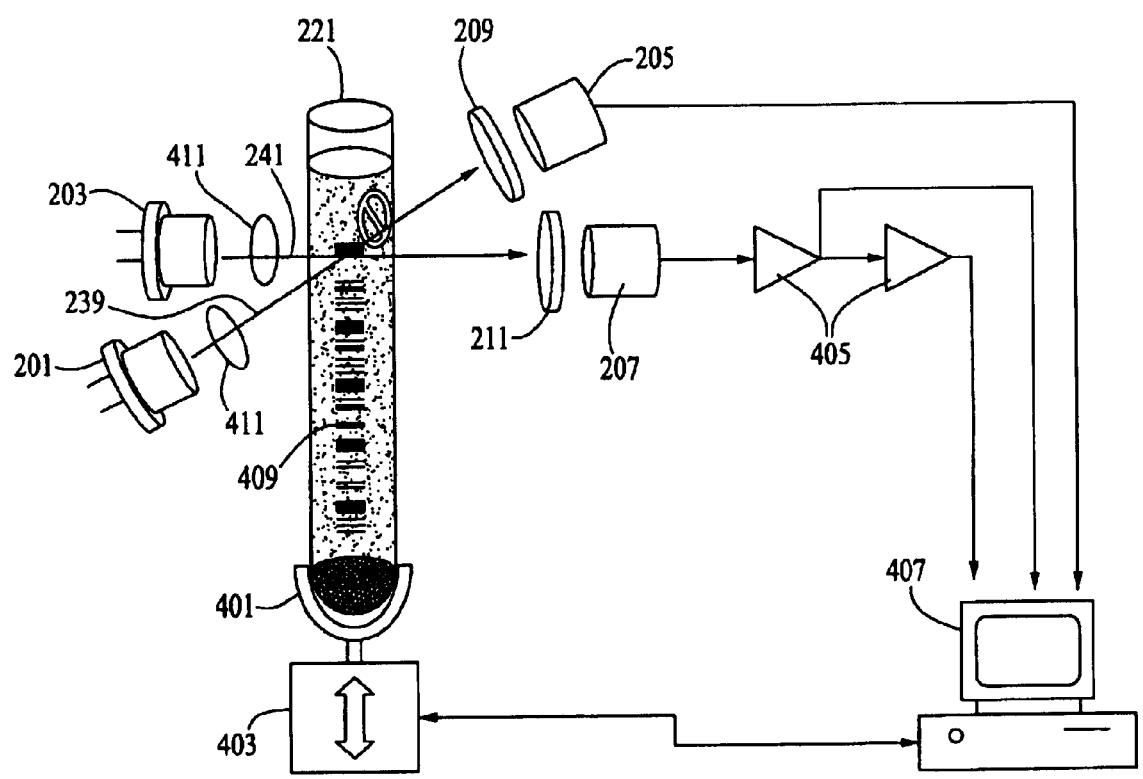
FIG. 4 is a front elevation view of a preferred version of a sample level detection system according to the present invention.

Preferably, the light sources 201 and 203 and detectors 209 and 211 are positioned so that the visible light detector 209 does not detect a significant amount of infrared light and the infrared light detector 211 does not detect a significant amount of visible light. This is preferably, but not necessarily, accomplished by having the light sources and the detectors be coplanar in a plane which is substantially perpendicular to the vertical axis 227 of the container, while angularly separating them as shown in FIGS. 2–4. For example, the light sources can be placed 90 degrees from each other in the same horizontal plane, while the detectors are placed directly opposite, i.e., 180 degrees from their respective light sources.

Referring now to FIG. 4 specifically, the test tube 221 having labels 409 sits on a tube holder 401 that is operably connected to a motion controller 403. As the motion controller 403 raises the test tube 221, the visible and infrared light beams 239 and 241, collimated by lenses 411 for greater label penetration, move down the tube. The detectors 205 and 207 detect the portions of the light beams 239 and 241 that pass through the tube 221 and its contents. The signal from the infrared light detector 207 passes through amplifiers 405 for dual gain before being analyzed, along with the signal from the visible light detector 205, by a personal computer 407.

The top of the serum 229 is detected when there is a characteristic drop in the infrared light reading 225 indicating that the infrared scan has moved from air to serum. The position of the top of the serum 229 is set where the readings 225 from the infrared detector 207 first fall dramatically and below a prescribed threshold.

Likewise, the top of the cells 237 is detected when there is a characteristic drop in the visible light reading 223 indicating that the visible scan has moved from serum 215 or gel 217 to cells 219. This drop is detected as the first incidence of readings 223 from the visible light detector 205 falls dramatically and below a prescribed threshold. The position of the top of the cells 237 is then set where readings 223 from the visible light detector 209 began their decent.

The infrared scan data within the range from the top of the cells 237 to the top of the serum 229 is investigated to determine if gel 217 is present in the container. If within this range, the infrared scan data contains a gel profile, a sufficiently high and sustained reading 225, then gel 217 is present in the container. In which case, the position of the top of the gel 233 is set to the position where the infrared reading 225 rose above a prescribed threshold. The position of the bottom of the gel 235 is set to same position as the top of the cells 237 and the position of the bottom of the serum 231 is set to the same position as the top of the gel 233. Otherwise the bottom of the serum 231 is set to the same position as the top of the cells 237.

Optionally, but not required, readings from both the visible and infrared channels are converted to log scale by applying a base 10 logarithm. If this is done before conversion, a constant is added to ensure the visible and infrared readings contain only positive data.

In order to reduce the effect of noise in the readings, a smoothing convolution filter (for example, the enhanced Savitzky Golay filter) can be used on the data.

Because the test tube 221 or other container may or may not have a cap 240 when scanned, a method of detecting and removing cap data can be used in conjunction with the invention. A cap 240 is detected when both the visible and infrared light readings 223 and 225 fall below prescribed thresholds during the initial portion of the scan. If a cap 240 is detected, an algorithm may be used to remove the position locations, visible light readings, and infrared light readings associated with the scan of the tube cap.

Error checking is preferably, but not necessarily, used in conjunction with the invention. Examples of some checks that may be used are: an algorithm that identifies excessively thick, narrow labeling, known as "strips", by searching the infrared channel for approximately 5 ml length drops; an algorithm that checks for gel widths outside of the expected range (generally, gels are approximately 12 ml, some have a double width of approximately 25 ml); if gel is detected, an algorithm that verifies the position of the top of the cells as found by the visible channel agrees with the position of the bottom of the gel found in the infrared channel. These three checks may spawn a change to the data by removing strips or iteration of the gel checking procedure.

Figure 6:
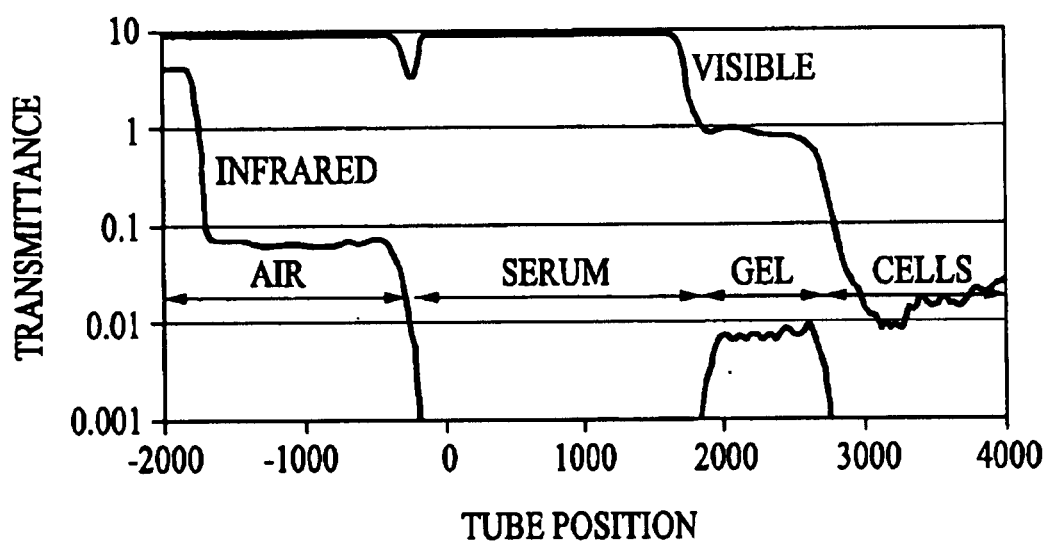
FIG. 6 is a graphical representation of a study that utilized the present invention.

The results of an experimental study are graphically illustrated in FIG. 6. Use of visible and infrared light gave the sample readings shown. The error rate was low. Approximately 800 sample tubes were tested resulting in a 3% error rate. However, when there was at least one label in the infrared light path, the error rate was 0% in the experimental study.

Although the present invention has been described in considerable detail with reference to certain preferred version thereof, other versions are possible. For example, the test tube or container can be stationary while the light sources and the light detector move along the vertical axis of the tube or container. Also, in some instances the container can contain no cells and no gel, and thus the only interface detected is the one between plasma or serum and the air in the container. Therefore, the spirit and scope of the appended claims should not necessarily be limited to the description of the preferred versions contained herein.

All features disclosed in the specification, including the claims, abstracts, and drawings, and all the steps in any method or process disclosed, may be combined in any combination, except combinations where at least some of such features and/or steps are mutually exclusive. Each feature disclosed in the specification, including the claims, abstract, and drawings, can be replaced by alternative features serving the same, equivalent or similar purpose, unless expressly stated otherwise. Thus, unless expressly stated otherwise, each feature disclosed is one example only of a generic series of equivalent or similar features.

Any element in a claim that does not explicitly state "means" for performing a specified function or "step" for performing a specified function, should not be interpreted as a "means" for "step" clause as specified in 35 U.S.C. §112.

What is claimed is:

1. A method for detecting the location of at least one interface in a container made up of a material and having a vertical axis and containing at least one layer of serum, plasma, and cells, the method comprising the steps of:

a) projecting onto the container a first detecting light beam having a first wavelength, the first detecting light beam being that substantially transmitted by serum, plasma, and the material but substantially blocked by cells, a portion of the first detecting light beam being transmitted through the container;

b) projecting onto the container a second detecting light beam having a second wavelength being different than the first wavelength, the second detecting light beam being substantially blocked by serum, plasma, and cells, but is substantially transmitted by the material, a portion of the second detecting light beam being transmitted through the container;

c) detecting, as a functiou of position along the vertical axis of the container, the portion of the first detecting light beam that is transmitted through the container and no significant portion of the second detecting light beam;

d) detecting, as a function of position along the vertical axis of the container, the portion of the second detecting light beam that is transmitted through the container and no significant portion of the first detecting light beam; and e) determining the location of at least one interface from the detected portions of the first and second detecting light beams.

2. The method of claim 1 wherein the material is plastic.

3. The method of claim 1 wherein the material is glass.

4. The method of claim 1 wherein the container is a test tube.

5. The method of claim 1 wherein the container contains an upper layer of plasma or serum, and a lower layer of cells.

6. The method of claim 1 or 5 wherein a plurality of labels are on the container.

7. The method of claim 5 wherein the container further contains a middle layer of gel between the layer of serum or plasma and the layer of cells, and both light beams are substantially transmitted by the gel.

8. The method of claim 1 wherein the first and second detecting light beams are projected by a projector and detected by a detector and wherein the projector and detector are substantially aligned so that the light beams strike the container substantially perpendicular to the axis of the container.

9. The method of claim 1 wherein a cap is covering the container.

10. The method of claim 1 wherein the light beams are projected by a laser.

11. The method of claim 1 wherein the light beams are projected by fiber optic cables.

12. The method of claim 1 wherein the location of the interface that is determined is the location between air and the contents of the container.

13. A method for detecting the location of at least one interface in a container made up of a material end having a vertical axis and containing an upper layer of at least one of serum and plasma and a lower layer of cells, the method comprising the steps of:
   a) projecting onto the container a first detecting light beam of visible light being substantially transmitted by serum, plasma, and the material, but substantially blocked by the cell, a portion of the first detecting light beam being transmitted through the container;
   b) projecting onto the container a second detecting light beam of infrared light being substantially blocked by serum, plasma, and cells, but is substantially transmitted, by the material, a portion of the second detecting light beam being transmitted through the container;
   c) detecting, as a function of position along time vertical axis of the container, the portion of the first detecting light beam that is transmitted through the container and no significant portion of the second detecting light beam;
   d) detecting, as a function of position along the vertical axis of the container, the portion of the second detecting light beam that is transmitted through the container and no significant portion of the first detecting light beam; and
   e) determining the location of at least one interface from the detected portions of the first and second detecting light beams.

14. The method of claim 13 wherein the container contains a layer of gel between the two layers, and wherein the gel is substantially transparent to the first and second detecting light beams.

15. The method of claim 14 wherein the container has at least one label on its exterior that obscures at least one interface.

16. The method of claim 13 wherein the wavelength of the first light beam is from about 300 nm to about 1200 nm.

17. The method of claim 13 or 16 wherein the wavelength of the second light beam is from about 1.4 pm to about 2.8 $\mu$m.

18. The method of claim 13 or 16 wherein the wavelength of the second light beam is from about 3.8 $\mu$m to about 68 $\mu$m.

19. A system for detecting the location of at least one interface in a container made up of a material and having a vertical axis and containing an upper layer of at least one of serum and plasma and a lower layer of cells, the system comprising:
   a) a first light source for projecting onto the container a first detecting light beam of visible light being that is substantially transmitted by serum, plasma, and the material but substantially blocked by the cells;
   b) a second light source for projecting onto the container a second detecting light beam of infrared light being substantially blocked by serum, plasma, and cells but substantially transmitted by the material;
   c) a first detector for detecting as a function of position along the vertical axis of the container, any portion of the first detecting light beam that is transmitted through the container and no significant portion of the second detecting light beam;
   d) a second detector for detecting as a function of position along the vertical axis of the container, any portion of the second detecting light beam that is transmitted through the container and no significant portion of the first detecting light beam; and
   e) a processor for determining the location of at least one interface from the detected portions of the first and second detecting light beams.

20. The system of claim 19 wherein the wavelength of the first light beam is from about 300 nm to about 1200 nm.

21. The system of claim 19 or 20 wherein the wavelength of the second light beam is from about 1.4 $\mu$m to about 2.8 $\mu$m.

22. The system of claim 19 or 20 wherein the wavelength of the second light beam is from about 3.8 $\mu$m to about 6.8 $\mu$m.

23. An apparatus for detecting the location of at least one interface in a container made up of a material and having a vertical axis and containing at least one layer of serum, plasma, and cells, comprising:
   a) a first projector that projects onto the container a first detecting light beam having a first wavelength, the first detecting light beam being substantially transmitted by serum, plasma, and the material but substantially blocked by cells, a portion of the first detecting light beam being transmitted through the container;
   b) a second projector that projects onto the container a second detecting light beam having a second wavelength being different than the first detecting light beam, the second detecting light beam being substantially blocked by serum, plasma, and cells but substantially transmitted by the material, a portion of the second detecting light beam being transmitted through the container;
   c) a first detector that detects, as a function of position along the vertical axis of the container, the portion of the first detecting light beam that is transmitted through the container;
   d) a second detector that detects, as a function of position along the vertical axis of the container, the portion of the second detecting light beam that is transmitted through the container; and
   e) a processor that is operably attached to the detectors and determines the location of the interfaces from the detected portions of the first and second detecting light beams.

24. A method for detecting the location of the interfaces in a container made up of a material and having a vertical axis and containing an upper layer of serum or plasma, a middle layer of gel, and a lower layer of cells, the method comprising the steps of:
   a) projecting onto the container a detecting light beam of infrared light being substantially blocked by serum or plasma and the cells but substantially transmitted by the material and the gel, a portion of the detecting light beam being transmitted through the container;
   b) detecting, as a function of position along the vertical axis of the container, the portion of the detecting light beam that is transmitted through the container; and
   c) determining the location of the interfaces from the detected portions of the detecting light beam.

25. A method for detecting the location of at least one interface in a container made up of a material and having a vertical axis and containing at least one layer of serum or plasma, the method comprising the steps of:
   a) projecting onto the container a first detecting light beam having a first wavelength the first detecting light beam being substantially transmitted by the serum or plasma, and the material, a portion of the first detecting light beam being transmitted through the container;

b) projecting onto the container a second detecting light beam having a wavelength different than the first detecting light beam, the second detecting light beam being substantially blocked by the serum or plasma, but substantially transmitted by the material, a portion of the second detecting light beam being transmitted through the container;

c) detecting, as a function of position along the vertical axis of the container, the portion of the first detecting light beam that is transmitted through the container and no significant portion of the second detecting light beam;

d) detecting, as a function of position along the vertical axis of the container, the portion of the second detecting light beam that is transmitted through the container and no significant portion of the first detecting light beam; and e) determining the location of at least one interface from the detected portions of the first and second detecting light beams.

* * * * *